(12) United States Patent
Liu et al.

(10) Patent No.: US 9,896,678 B2
(45) Date of Patent: Feb. 20, 2018

(54) MUTANT WITH ENHANCED SECRETION OF L-ASPARAGINASE AND ITS APPLICATION

(71) Applicant: Jiangnan University, Wuxi (CN)

(72) Inventors: Song Liu, Wuxi (CN); Yue Feng, Wuxi (CN); Jian Chen, Wuxi (CN); Guocheng Du, Wuxi (CN); Yun Jiao, Wuxi (CN); Jie Ruan, Wuxi (CN); Hongye Cheng, Wuxi (CN); Hui Gao, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 40 days.

(21) Appl. No.: 15/189,139

(22) Filed: Jun. 22, 2016

(65) Prior Publication Data
US 2017/0145401 A1    May 25, 2017

(30) Foreign Application Priority Data
Nov. 25, 2015  (CN) .......................... 2015 1 0837174

(51) Int. Cl.
*C12N 9/82* (2006.01)
*A61K 38/00* (2006.01)

(52) U.S. Cl.
CPC ........ *C12N 9/82* (2013.01); *C12Y 305/01001* (2013.01); *A61K 38/00* (2013.01)

(58) Field of Classification Search
None
See application file for complete search history.

(56) References Cited

U.S. PATENT DOCUMENTS

2003/0186380 A1* 10/2003 Thomas ......... C12Y 305/01001
435/69.1

OTHER PUBLICATIONS

GenBank Accession No. AFQ56204.1, published Jan. 31, 2014.*

* cited by examiner

*Primary Examiner* — Richard Ekstrom
(74) *Attorney, Agent, or Firm* — IPro, PLLC; Na Xu; Qian Gu

(57) ABSTRACT

The present invention provides a mutant with enhanced secretion of L-asparaginase and its application, which relates to the field of enzyme engineering. This invention successfully constructed a mutant with enhanced secretion of L-asparaginase through N-terminal deletion on amino acid sequence of L-asparaginase, and then expressed the mutant via a recombinant strain. Compared with the wild L-asparaginase, the secretion ability of L-asparaginase mutant in present invention significantly improves by 3.14 times compared to that of wild type. The recombinant strain that constructed in this prevention has an L-asparaginase yield of 407.6 U/mL and a production efficiency of 9.26 U/(mL/h), which reaches to the highest yield been reported.

2 Claims, 2 Drawing Sheets

SEQUENCE LISTING

```
<160> NUMBER OF SEQ ID NOS: 6

<210> SEQ ID NO 1
<211> LENGTH: 370
<212> TYPE: PRT
<213> ORGANISM: Artificial Sequence
<220> FEATURE:
<223> OTHER INFORMATION: Protein translated from synthetic DNA

<400> SEQUENCE: 1

Met Lys Lys Arg Lys Arg Arg Asn Phe Lys Arg Phe Ile Ala Ala Phe
1               5                   10                  15

Leu Val Leu Ala Leu Met Ile Ser Leu Val Pro Ala Asp Val Leu Ala
            20                  25                  30

Lys His His His His His Ser Glu Lys Lys Asp Leu Pro Asn Ile
        35                  40                  45

Arg Ile Leu Ala Thr Gly Gly Thr Ile Ala Gly Ala Asp Gln Ser Lys
    50                  55                  60

Thr Ser Thr Thr Glu Tyr Lys Ala Gly Val Val Gly Val Glu Ser Leu
65                  70                  75                  80

Ile Glu Ala Val Pro Glu Met Lys Asp Ile Ala Asn Val Ser Gly Glu
                85                  90                  95

Gln Ile Val Asn Val Gly Ser Thr Asn Ile Asp Asn Lys Ile Leu Leu
            100                 105                 110

Lys Leu Ala Lys Arg Ile Asn His Leu Leu Ala Ser Asp Asp Val Asp
        115                 120                 125

Gly Ile Val Val Thr His Gly Thr Asp Thr Leu Glu Glu Thr Ala Tyr
    130                 135                 140

Phe Leu Asn Leu Thr Val Lys Ser Asp Lys Pro Val Val Ile Val Gly
145                 150                 155                 160

Ser Met Arg Pro Ser Thr Ala Ile Ser Ala Asp Gly Pro Ser Asn Leu
                165                 170                 175

Tyr Asn Ala Val Lys Val Ala Gly Ala Pro Glu Ala Lys Gly Lys Gly
            180                 185                 190

Thr Leu Val Val Leu Asn Asp Arg Ile Ala Ser Ala Arg Tyr Val Thr
        195                 200                 205

Lys Thr Asn Thr Thr Thr Asp Thr Phe Lys Ser Glu Glu Met Gly
    210                 215                 220

Phe Val Gly Thr Ile Ala Asp Asp Ile Tyr Phe Asn Asn Glu Ile Thr
225                 230                 235                 240
```

```
Arg Lys His Thr Lys Asp Thr Asp Phe Ser Val Ser Asn Leu Asp Glu
            245                 250                 255

Leu Pro Gln Val Asp Ile Ile Tyr Gly Tyr Gln Asn Asp Gly Ser Tyr
        260                 265                 270

Leu Phe Asp Ala Ala Val Lys Ala Gly Ala Lys Gly Ile Val Phe Ala
            275                 280                 285

Gly Ser Gly Asn Gly Ser Leu Ser Asp Ala Ala Glu Lys Gly Ala Asp
        290                 295                 300

Ser Ala Val Lys Lys Gly Val Thr Val Val Arg Ser Thr Arg Thr Gly
305                 310                 315                 320

Asn Gly Val Val Thr Pro Asn Gln Asp Tyr Ala Glu Lys Asp Leu Leu
            325                 330                 335

Ala Ser Asn Ser Leu Asn Pro Gln Lys Ala Arg Met Leu Leu Met Leu
            340                 345                 350

Ala Leu Thr Lys Thr Asn Asp Pro Gln Lys Ile Gln Ala Tyr Phe Asn
            355                 360                 365

Glu Tyr
    370

<210> SEQ ID NO 2
<211> LENGTH: 1113
<212> TYPE: DNA
<213> ORGANISM: Artificial Sequence
<220> FEATURE:
<223> OTHER INFORMATION: Synthetic DNA

<400> SEQUENCE: 2
atgaaaaaaa gaaagaggcg aaactttaaa aggttcattg cagcattttt agtgttggct        60
ttaatgattt cattagtgcc agccgatgta ctagcaaaac accaccacca ccaccactct       120
gaaaaaaagg atctgccaaa cattagaatt ttagcgacag gaggcacgat agctggtgcc       180
gatcaatcga aaacctcaac aactgaatat aaagcaggtg ttgtcggcgt tgaatcactg       240
atcgaggcag ttccagaaat gaaggacatt gcaaacgtca gcggcgagca gattgttaac       300
gtcggcagca caaatattga taataaaata ttgctgaagc tggcgaaacg catcaaccac       360
ttgctcgctt cagatgatgt agacggaatc gtcgtgactc atggaacaga tacattggag       420
gaaaccgctt attttttgaa tcttaccgtg aaaagtgata accggttgt tattgtcggt       480 tcgatgagac cttccacagc catcagcgct gatgggcctt ctaacctgta caatgcagtg       540
aaagtggcag gtgcccctga ggcaaaaggg aaagggacgc ttgttgttct aacgaccgg        600 attgcctcag cccgatatgt caccaaaaca acacaactca aacagatac atttaaatca       660 gaagaaatgg gcttcgtcgg aacaattgca gatgatatct attttaataa tgagattacc       720
cgtaagcata cgaaggacac ggatttctcg gtttctaatc ttgatgagct gccgcaggtt       780
gacattatct atggatacca aaatgacgga agctacctgt ttgacgctgc tgtaaaagcc       840
ggagcaaagg ggattgtatt tgccggttct gggaacgggt cttatctga tgcagccgaa       900 aaaggggcgg acagcgcagt caaaaaggc gttacagtgg tgcgctctac ccgcacggga       960
aatggtgtcg tcacaccaaa ccaagactat gcggaaaagg acttgctggc atcgaactct      1020
ttaaaccccc aaaaagcacg gatgttgctg atgcttgcgc ttaccaaaac aaatgatcct      1080
caaaaaatcc aagcttattt caatgagtat tga                                    1113

<210> SEQ ID NO 3
<211> LENGTH: 57
<212> TYPE: DNA
```

```
<213> ORGANISM: Artificial Sequence
<220> FEATURE:
<223> OTHER INFORMATION: Synthetic DNA

<400> SEQUENCE: 3
cggggtacca ttataggtaa gagaggaatg tacacatgaa aaaagaaag aggcgaa        57

<210> SEQ ID NO 4
<211> LENGTH: 35
<212> TYPE: DNA
<213> ORGANISM: Artificial Sequence
<220> FEATURE:
<223> OTHER INFORMATION: Synthetic DNA

<400> SEQUENCE: 4
aaaactgcag ggatcctcta gagattcgcc ctagg                              35

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA

<400> SEQUENCE: 5
tctgaaaaaa aggatctgcc aa                                            22

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
gtggtggtgg tggtggtgtt                                               20
```

MUTANT WITH ENHANCED SECRETION OF L-ASPARAGINASE AND ITS APPLICATION

CROSS-REFERENCES AND RELATED APPLICATIONS

This application claims the benefit of priority to Chinese Application No. 201510837174.8, entitled "A mutant with enhanced secretion of L-asparaginase and its application", filed Nov. 25, 2015, which is herein incorporated by reference in its entirety.

BACKGROUND OF THE INVENTION

Field of the Invention

The present invention relates to the field of enzyme engineering, which relates to a mutant with enhanced secretion of L-asparaginase and its application.

Description of the Related Art

L-asparaginase (EC3.5.1.1) is an enzyme used effectively in the treatment of cancer. It catalyzes the hydrolysis of amino acid L-asparagine to aspartic acid and ammonia. L-asparaginase has been proved to have inhibitive activity on tumor cells, especially on acute leukemia and malignant lymphoma. Besides the cancer-combating properties and no inhibitory on bone marrow cells, L-asparaginase is employed as effective drugs in the treatment of acute lymphoblastic leukemia (ALL).

Two forms of L-asparaginases have been reported, namely L-asparaginase I and L-asparaginase II. The properties of these two enzymes, especially enzymes from *Escherichia coli*, *Erwinia carotovora*, and *Erwinia chrysanthemi*, have been studied intensively. Since it has been proved that only L-asparaginase II has cancer-combating properties, most research is about L-asparaginase II. L-asparaginase II produced by *Escherichia coli* and *Erwinia chrysanthemi* has already been developed into drugs for acute lymphoblastic leukemia treatment.

Acrylamide is formed through Maillard reaction which happens when sugars and asparagine are heated under high temperature. L-asparaginase can reduce the content of acrylamide in food.

L-asparaginase has been widely found in microbials, mammals and plants. Compared with the low content of L-asparaginase in animal serum, and the complex extraction process, there are advantages of L-asparaginase produced by means of microorganism fermentation, including easy cultivation and low costs. Current L-asparaginase is mainly produced by microorganisms including *Escherichia coli*, *Erwinia carotovora*, *Erwinia chrysanthemi*, etc. However L-asparaginase shows low yield in wild strains. In recent years, high efficient expression of L-asparaginase has become an important source for L-asparaginase production, which is realized by *Escherichia coli* expressed L-asparaginase gene.

However, the critical problem to be solved is to realize L-asparaginase expression in food safety strains and improve its secretion.

DETAILED DESCRIPTION

The goal of the present invention is to realize the L-asparaginase expression in *Bacillus subtilis* through a strong promoter p43 and an efficient secretory signal peptide. Furthermore, certain amino acids located in the N-terminal of L-asparaginase are truncated to promote the expression of L-asparaginase.

The first goal of the present invention is to provide a mutant with enhanced secretion of L-asparaginase, wherein the mutant comprises an amino acid sequence as shown in SEQ ID NO.1. The L-asparaginase mutant carries an exogenous signal peptide WapA that replaces the original signal peptide in nature L-asparaginase (NCBI No. NC-000964.3), and the N-terminal of the L-asparaginase mutant is deleted.

The mutant has an nucleotide sequence as shown in SEQ ID NO.2.

The second goal of the present invention is to provide a recombinant *Bacillus subtilis* which expresses the gene encoding L-asparaginase mutant via plasmid pP43NMK.

In one embodiment of the present invention, the L-asparaginase mutant gene carries nucleotides encoding exogenous signal peptide WapA.

In one embodiment of the present invention, the host of recombinant *Bacillus subtilis* is *Bacillus subtilis* WB600.

In one embodiment of the present invention, the L-asparaginase mutant gene comprises an amino acid sequence as shown in SEQ ID NO.2.

In one embodiment of the present invention, the L-asparaginase mutant gene is ligated to pP43NMK by restriction enzyme sites Kpn and Pst I and then transferred into *Bacillus subtilis* WB600.

The third goal of the present invention is to provide a method for producing L-asparaginase by the recombinant *Bacillus subtilis*. The seed culture is inoculated to the fermentation medium at an inoculation percent of 4% (v/v) and then cultivated at 37° C. to produce L-asparaginase.

In one embodiment of the present invention, the wherein method is carried out through maintaining the medium pH at 7.0 and maintaining dissolved oxygen at above 20%, and maintaining high density fermentation by adding sucrose and peptone during fermentation process.

The present invention provided a mutant with enhanced secretion of L-asparaginase through N-terminal deletion and a recombinant strain to express the mutant. Compared with the wild L-asparaginase, the secretion ability of L-asparaginase mutant in present invention significantly improves by 3.14 times. The recombinant in this invention has an L-asparaginase yield of 407.6 U/mL and a production efficiency of 9.26 U/(mL·h), which is the highest yield so far. The L-asparaginase production of the present invention is 4.5 times higher than the production of the recombinant *Bacillus subtilis* which expressed the L-asparaginase gene with wild type signal peptide (Cloning, expression, and characterization of L-asparaginase from a newly isolated *Bacillus subtilis* B11-06), and 8.71 times higher than that of recombinant *E. coli* (CN 201510102732.6).

DETAILED DESCRIPTION

Figure 1:
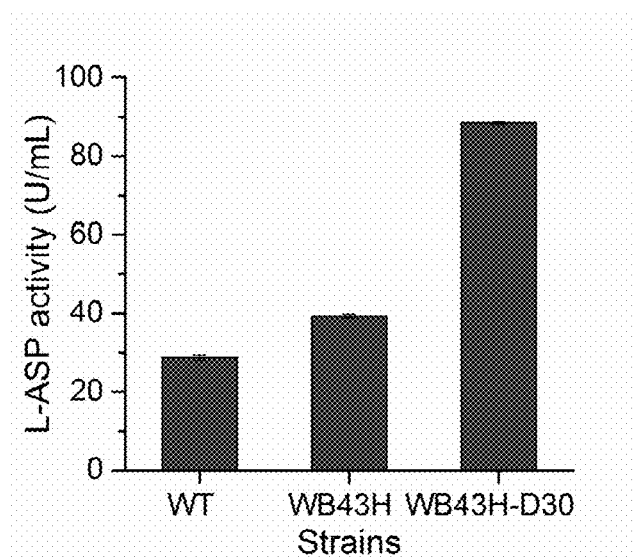
FIG. 1 illustrates the L-asparaginase activity of mutants.

Materials and Methods:

Medium:

LB medium: peptone 10 g/L, yeast extract 5 g/L, NaCl 10 g/L, pH was adjusted to 7.0.

Fermentation medium: soybean peptone 10 g/L, corn pulp 5 g/L, urea 1 g/L, sucrose 35 g/L, $K_2HPO_4$ 2.3 g/L, $KH_2PO_4$ 1.7 g/L, $MgSO_4$ 0.75 g/L, NaCl 5 g/L, pH was adjusted to 6.8-7.0.

Enzyme Assay:

L-asparaginase activity was determined by a spectrophotometric assay using asparagine as the substrate. One unit of enzyme was defined as the amount of enzyme that catalyzed the formation of 1 µmol $NH_3$ per minute.

The standard assay comprised following steps: 1 mL 10 mmol/L $K_2HPO_4$—$KH_2PO_4$ (pH 7.5), 0.1 mL 189 mmol/L asparagine and 0.1 mL enzyme solution were mixed and incubated at 37° C. for 30 min. Then 0.5 mL 1.5 mmol/L TCA was added to terminate the reaction. The formation of $NH_3$ was spectrophotometrically monitored at 436 nm by ShimadzuUV-1240. Enzyme activity was calculated according to the standard curve that obtained by $(NH_4)_2SO_4$ detection.

EXAMPLE 1

Construction of Strain Possesses Strong Promoter with High Efficient Expression

Primers P1, P2 (shown in Table 1) were designed for amplifying gene L-ASP carrying signal peptide WapA. The plasmid pMA0911-wapA-SP-ansZ been constructed before was used as templates for amplifying gene L-ASP through polymerase chain reaction (PCR). The PCR cycle comprised: the first step at 98° C. for 3 minutes; 34 cycles of the second step at 98° C. for 30 seconds (denaturation), at 55° C. for 90 seconds (aling), and at 72° C. for 90 seconds (elongation). PCR was carried out using 50 µL of a reaction solution comprising 1 µL of each primer, 4 µL dNTP Mix, 10 µL 5×primeSTAR Buffer, 32.5 µL double distilled water, and 0.5 µL primeSTAR DNA polymerase.

The amplified DNA fragment was purified using gel extraction kit, DNA concentration of which was measured by agarose gel electrophoresis. The purified DNA fragment and plasmid pP43NMK was then cleaved at the restriction enzyme cleavage sites at both of its ends with Kpn I and Pst I. The resulting DNA fragment from L-ASP and pP43NMK was purified separately by gel extraction kit. DNA concentration were measured via agarose gel electrophoresis.

Subsequently, DNA fragments L-ASP were ligated to pP43NMK at a volume of 10 µL comprising 4 µL L-ASP, 1 µL carrier pP43NMK and 5 µL solution I. The ligation was carried out at 16° C. overnight then recombinant plasmid that designated as pP43H was obtained. The pP43H was then introduced into *E. coli* JM109. The resulting transformants were cultured on the LB agar containing ampicillin. Positive colonies were picked and plasmids of which were extracted. Transformants having a plasmid of interest were identified based on the restriction enzyme cleavage patterns and via nucleotide sequence analysis. The recombinant plasmids WB43H were constructed through transforming pP43H into *Bacillus subtilis* commensurately according to above procedures.

TABLE 1

| Name | Sequence | Number |
|------|----------|--------|
| P1 | CGGGGTACCATTATAGGTAAGAGAGGAATGTA CACATGAAAAAAAGAAAGAGGCGAA | SEQ ID NO. 3 |
| P2 | AAAACTGCAGGGATCCTCTAGAGATTCGCCCT AGG | SEQ ID NO. 4 |
| P3 | TCTGAAAAAAAGGATCTGCCAA | SEQ ID NO. 5 |
| P4 | GTGGTGGTGGTGGTGGTGTT | SEQ ID NO. 6 |

EXAMPLE 2

Construction of Strains with Truncated N-Terminal

Primers P3, P4 (shown in Table 1) were designed, plasmid pP43H was used as templates for amplifying truncated N-terminal DNA fragments through PCR. The PCR cycle comprised: the first step at 98° C. for 3 minutes; 34 cycles of the second step at 98° C. for 30 seconds (denaturation), at 55° C. for 90 seconds (aling), and at 72° C. for 90 seconds (elongation). PCR was carried out using 50 µL of a reaction solution comprising 1 µL of each primer, 4 µL dNTP Mix, 10 µL 5×primeSTAR Buffer, 32.5 µL double distilled water, and 0.5 µL prime STAR DNA polymerase.

The resulting PCR amplicons were purified and measured by agarose gel electrophoresis. The purified DNA fragments were dephosphorylated and ligated at 16° C. overnight adding with DNA ligase. The recombinant plasmid that designated as D30 was introduced into competent *E. coli* JM109. The resulting transformants were cultured on the LB agar containing ampicillin at 37° C. overnight. Positive colonies were picked and plasmids of which were extracted. Transformants having a plasmid of interest were identified based on the restriction enzyme cleavage patterns and via nucleotide sequence analysis. The recombinant mutant WB43H-D30 with 25 N-terminal deletion of gene L-ASP were constructed through transforming pP43H into *Bacillus subtilis* WB600 commensurately according to above procedures.

EXAMPLE 3

Verification of Highly Secreted Strain for L-Asparaginase Production

The recombinant WB43H, WB43H-D30 (constructed in example 1 and example 2) and pMA0911-wapA-SP-ansZ/ *B.subtilis*WB600 (ZL201310716775.4) were inoculated in 10 mL LB medium containing kanamycin and shake cultured at 37° C. overnight. Culture broth were centrifuged at 4° C., 10000 r/min for 10 min, crude extracellular enzyme was obtained in supernatant, crude intracellular enzyme was obtained in supernatant of cell homogenates. Both extracellular and intracellular enzymes were used for enzyme assay.

Figure 2:
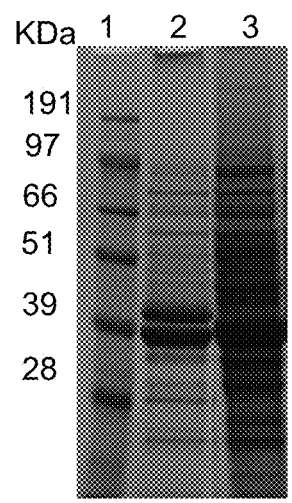
FIG. 2 illustrates results of SDS-PAGE analysis of L-asparaginase; 1. Wild type; 2, WB43H; 3, WB43H-D30.

The L-asparaginase activity was shown in FIG. 1. Compared with the wild type strain, the extracellular L-asparaginase activity in mutant WB43H was 39.52 U/mL, improved 1.4 times than that from the wild type; the extracellular L-asparaginase activity in mutant WB43H-D30 was 88.24 U/mL, improved 3.14 times than that from the wild type. The effect of improving L-asparaginase production through N-terminal deletion was further verified through SDS-PAGE analysis (FIG. 2).

EXAMPLE 4

Fed-Batch Fermentation for L-Asparaginase Production

Figure 3:
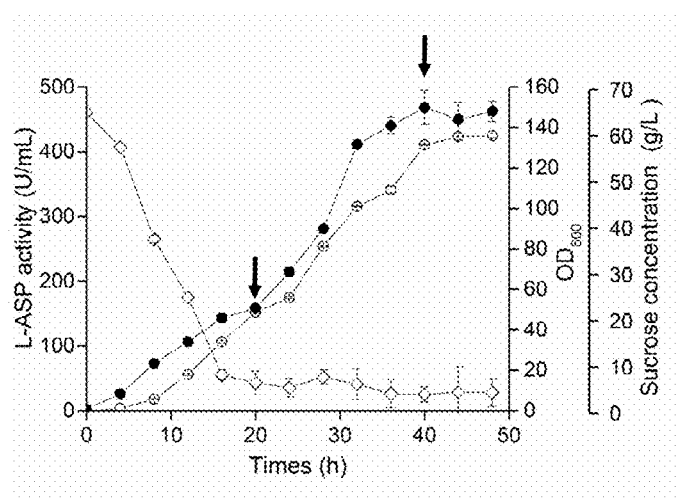
FIG. 3 illustrates time profiles for batch cultivation of recombinant D30 in 3 L fermenter; Open circles: the activity of asparaginase (U/mL); Closed circles: Cell growth; Open rhombus: Sucrose concentration (g/L).

The recombinant strain WB43H-D30 (constructed in example 2) was inoculated at an inoculation percent of 4% (v/v) and caltivated in 3-L fermentor to produce L-asparaginase. The initial medium has the same ingredient with the shake flask medium. The fermentation was carried out through maintaining pH at 7.0 by feeding acid and alkali, keeping the dissolved oxygen (DO) above 20% through controlling DO associating with agitation speed, and feeding sucrose and peptone for high density fermentation. As a result, the $OD_{600}$ of culture broth was 153 after fermented for 40 h, L-asparaginase yield reached to 407.6 U/mL while productivity reached to 9.26 U/(mL/h) when fermented for 44 h (FIG. 3). This yield is 4.5 times higher than that of *Bacillus subtilis* carrying wild type signal peptide and 8.71 times higher than that of recombinant *E. coli*, which is the highest yield been reported so far. This high yield of L-asparaginase also indicated the suitability of *Bacillus subtilis* as a host for L-asparaginase production.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. An L-asparaginase mutant comprising the amino acid sequence of SEQ ID NO.1.

2. An application of the L-asparaginase mutant of claim 1 in manufacturing medicine, comprising adding the L-asparaginase mutant into a predetermined formulation.

* * * * *